United States Patent [19]

Carollo et al.

[11] Patent Number: 4,604,649
[45] Date of Patent: Aug. 5, 1986

[54] RADIOGRAPHIC INSPECTION MEANS AND METHOD

[75] Inventors: Sammy F. Carollo, Irving; William E. Dance, Dallas, both of Tex.

[73] Assignee: Vought Corporation, Dallas, Tex.

[21] Appl. No.: 324,519

[22] Filed: Nov. 24, 1981

[51] Int. Cl.$^4$ .............................................. H04N 5/32
[52] U.S. Cl. .................... 358/111; 378/141; 250/238
[58] Field of Search ............... 358/111, 139, 110, 229, 358/227, 100, 221, 101, 107; 378/88, 59, 96, 99, 100, 141; 250/238, 239, 251, 213 VT

[56] References Cited

U.S. PATENT DOCUMENTS

| | | | |
|---|---|---|---|
| 2,690,516 | 9/1954 | Sheldon | 358/110 |
| 3,097,263 | 7/1963 | Lintern | 358/100 |
| 3,327,126 | 6/1967 | Shannon et al. | 250/238 |
| 3,891,852 | 6/1975 | Bollen et al. | 250/391 |
| 4,359,759 | 1/1982 | McBride | 358/111 |

FOREIGN PATENT DOCUMENTS 5147888 11/1980 Japan ................................. 358/111

OTHER PUBLICATIONS

Electronic Engineering, Jun. 1959, "A Large Screen X-Ray Image Amplifier".

Primary Examiner—Edward L. Coles, Sr.
Attorney, Agent, or Firm—James M. Cate; Stephen S. Sadacca

[57] ABSTRACT

A radiographic image is formed of a workpiece irradiated by neutron or X-ray energy. A radiophosphorescent screen is positioned adjacent the workpiece to form a scintillation pattern. The radiation may consist of thermal neutrons radiation from which gamma radiation has been substantially removed. The image is stored upon the semi-conductor target of a television camera.

36 Claims, 2 Drawing Figures

RADIOGRAPHIC INSPECTION MEANS AND METHOD

TECHNICAL FIELD

The present invention relates to radiographic imaging systems and, more particularly, to radiographic apparatus having means for producing images derived from radiation shadowgraphs derived with the use of neutron or X-radiation sources.

BACKGROUND ART

The forming and processing of radiographically produced shadowgraphs or radiation transmission patterns to produce visual images of a specimen or workpiece is of interest in various applications, such as the radiographic inspection of various structural components. Previously, such inspection techniques entailed the forming of photoshadowgraphs. A photographic film plate was positioned adjacent an object to be inspected by the neutron or X-ray source, the object being positioned between the film and the source of radiation. When neutron or X-radiation is transmitted through any hetrogeneous object, it is differentially absorbed, depending upon the varying thickness, density, and chemical composition of the object. The image registered by the emergent rays on a film adjacent to the specimen under examination constitutes a shadowgraph, or radiograph, i.e. an intensity pattern of the rays transmitted, of the interior of the specimen.

X-radiation may be used in industrial applications wherein, for example, it is desired to evaluate a metal casting suspected of having internal cracks, separations, voids, or other defects; and it is, of course, employed widely in medical applications. X-rays are, in general, substantially more penetrating than neutron radiation with respect to "low-z" materials such as aluminum, plastic, boron, carbon, and the like. Radiographs produced from neutron radiation are employed, for example, when it is desired to form an image of hydrogenous, or organic materials which may be present within metallic structures. Neutrons penetrate low-thermal-cross-section materials such as lead, aluminum, steel, and titanium, but are absorbed by organic, hydrogenous materials. With respect to metallic stuctural members, an indication of such hydrogenous materials within the structure may reveal the presence of water, hydroxides, and other corrosion products. Such corrosion may be in the form of intergranular corrosion, with accompanying exfoliation, of materials such as aluminum, and certain other metals. Stresses in aluminum aircraft components, for example, produce internal, intergranular corrosion which is invisible and not accurately imaged by conventional, non-destructive inspection techniques; such corrosion may result in critical failure of major structural elements if it continues undetected. As in the design of load-bearing or structural members for various industrial applications, the conventional design philosophy for aerospace components entails a substantial degree of "over design" for ensuring structural integrity of the components. As will be understood by those in the art, such an excess of material results in correspondingly higher weight and cost, and in lower performance and fuel efficiency than would be obtained if compensation for potential, undetectable internal deterioration was not necessary. Similarly, the permissible useful life of such components is also based upon safety margins which can be substantially reduced if positive assurance were obtainable that internal, or hidden deterioration had not occurred to a significant degree.

Further difficulties with respect to non-destructive testing of aerospace components relate to the possibilities of surface corrosion on internal components hidden from visual inspection. Corrosion which may occur within honeycomb cell ctructures or panels may result in the separation of honeycomb cores from outer skin surfaces, and the like.

In the past it has been attempted to produce images produced from low level radiation such as neutron, or low level X-radiation, by exposing photographic films to the radiation for an appropriate period of time and developing the film for inspection. The use of photographic film provides the advantage that, through exposure over an extended period of time, very low levels of radiation may form a satisfactory photoradiograph. Exposure times, film speed, radiation levels and film types may be varied. It will be understood, however, that the delays entailed in set-up and film processing imparts limitations in inspection efficiency, particularly when it is desired to inspect, and reinspect, large components or large numbers of components. For this reason, modern radiographic inspection systems have employed low-light-level television cameras for producing television images derived from the radiation of a specimen, whereby a television display corresponding to a radiophotograph is formed. The television monitor may be located in a facility remote from the radiation source, which may afford advantages when hazardous radiation is present. Additionally, television monitoring permits continuous monitoring of a component for real, or "near real time" examination. Such low-light-level television cameras may be of the image orthicon type or of other types, and often employ multiple stages of image intensification or amplification. Modern, low-light-level cameras include various refinements and intensification techniques, such as silicon intensified targets (SIT), secondary electron conduction (SEC), charge-storing, and amplifying.

Two general approaches to the formation of television images of irradiated specimens are illustrated in U.S. Pat. Nos. 3,280,253 and 3,668,396, to R. C. McMaster et al and J. A. Asars et al, respectively, both of which are hereby incorporated by reference. The system of the McMaster patent employs a single stage camera tube which is sensitive to X-radiation. In use, a radiation source is positioned to direct X-radiation directly toward the television camera tube after transmission through a workpiece to be inspected, and an image is formed on the camera tube target by electrons derived from the X-radiation directed toward the camera; the image is intensified by the use of periodic beam scanning, in which the radiation builds up adequate image potential (an image pattern comprising a loss of positive charges at portions of a semiconductor target) between raster scanning cycles. A satisfactory TV image is produced by intermittent scanning of the target by the electron beam raster scanner. The McMaster camera includes no intermediate intensifying stages. Such single stage camera tubes provide relatively moderate gain in comparison with highly sensitive tubes such as that disclosed in the recent Asars patent. The McMaster system may thus be considered to have a relatively high level of input radiation (radiation directly from the X-ray source, which is of generally higher intensity and penetrating potential than portable neutron sources) and a relatively low level of internal intensification or amplification in comparison with multi-stage cameras such as that disclosed in the Asar patent. Such systems are advantageous for certain applications, and such single stage television cameras are less expensive and complex than multi-stage, very low-light-level cameras.

The Asars system employs a phosphor screen to provide a large field of view of appropriate resolution and detail, the phosphor screen serving to generate scintillations of light as the screen receives gamma radiation derived from a neutron source. The light scintillations on the screen are detected and intensified through the sensitive, multi-stage SEC camera tube. To provide adequate light amplification, the camera tube employs several stages of image intensification, including an initial image intensifier tube section and an intermediate image intensifying section. As will be understood by those in the art, sophisticated low-light level cameras such as that employed in the Asars system are highly complex and expensive.

The present system is intended to provide a radiographic television display with a relatively lower cost and less complex camera system, while at the same time providing very high sensitivity to low radiation levels. In particular, it is intended to provide a radiographic system sensitive to "soft" or thermal neutron radiation, i.e., radiation from which the higher energy neutron and gamma rays have been removed, as may be obtained from portable radiographic generator systems such as that disclosed in U.S. Pat. No. 4,300,054, issued Nov. 10, 1981, to W. E. Dance et al, which is incorporated by reference. The system of the U.S. Pat. No. 4,300,054 employs a modulator fluid and filter for attenuating the hard, gamma radiation from energy produced by a radiation generator tube. There is a need, particularly in the inspection of aircraft and other components by low power, non-isotopic radiation sources, for an efficient television radiographic display means wherein a high resolution image is produced for convenient viewing. In such systems, radioactive isotopes as radiographic sources are not employed, eliminating the hazards and inconveniences entailed in the transportation and storage of such materials.

A problem entailed in prior radiographic systems has been difficulty in producing a high resolution, finely detailed image in the presence of varying levels of radiation. High radiation peaks may tend to overload and blur the camera and may even damage the camera. Another problem has been that very low levels of radiation, such as those obtained from thermal neutron sources and from low level X-rays, have been difficult to record because of inherent system noise. The obtaining of detailed images required to show fissures and details of internal deterioration of metals with sufficient resolution to ensure that no critical faults exist in a piece under inspection is of importance in many applications. A further deficiency in prior inspection systems has been their limitation to undesirably narrow ranges of energy levels. That is, those instruments sensitive to high level radiation such as that produced by X-radiation have been insensitive and not usable with lower levels of radiation commonly received as neutron radiation. Prior systems were not usable with low-level neutron radiation.

DISCLOSURE OF THE INVENTION

It is, accordingly, a major object of the present invention to provide a new and improved radiographic imaging system.

Another object is to provide such an imaging system which is sensitive to relatively low levels of radiation, including thermal neutron radiation free of any substantial gamma radiation. A still further object is to provide such a system which is operable to produce images of high resolution derived from thermal neutron radiation of, for example at least about 100 neutrons per square cm. per second and X-rays of low and very high levels.

Yet another object is to provide such an imaging system which is usable to provide high resolution television images, and which can provide such images derived from shadowgraphs produced by both neutron and X-radiation.

A further object is to provide such an imaging system in which highly complex, low-light-level television cameras with multiple stages of intensification are not required, yet which provides an overall radiographic sensitivity comparable to or greater than such prior systems.

Yet another object is to provide such a system in which the television image produced is free of any substantial noise and distortion, wherein highly detailed images may be displayed permitting accurate inspection of components for small cracks, voids, fissures, and other similar faults.

Yet another object is to provide such an imaging system which is of practicable, relatively straightforward and inexpensive construction, permitting convenient portability.

Other objects and advantages will be apparent from the specification and claims and from the accompanying drawing illustrative of the invention.

DETAILED DESCRIPTION

Figure 1:
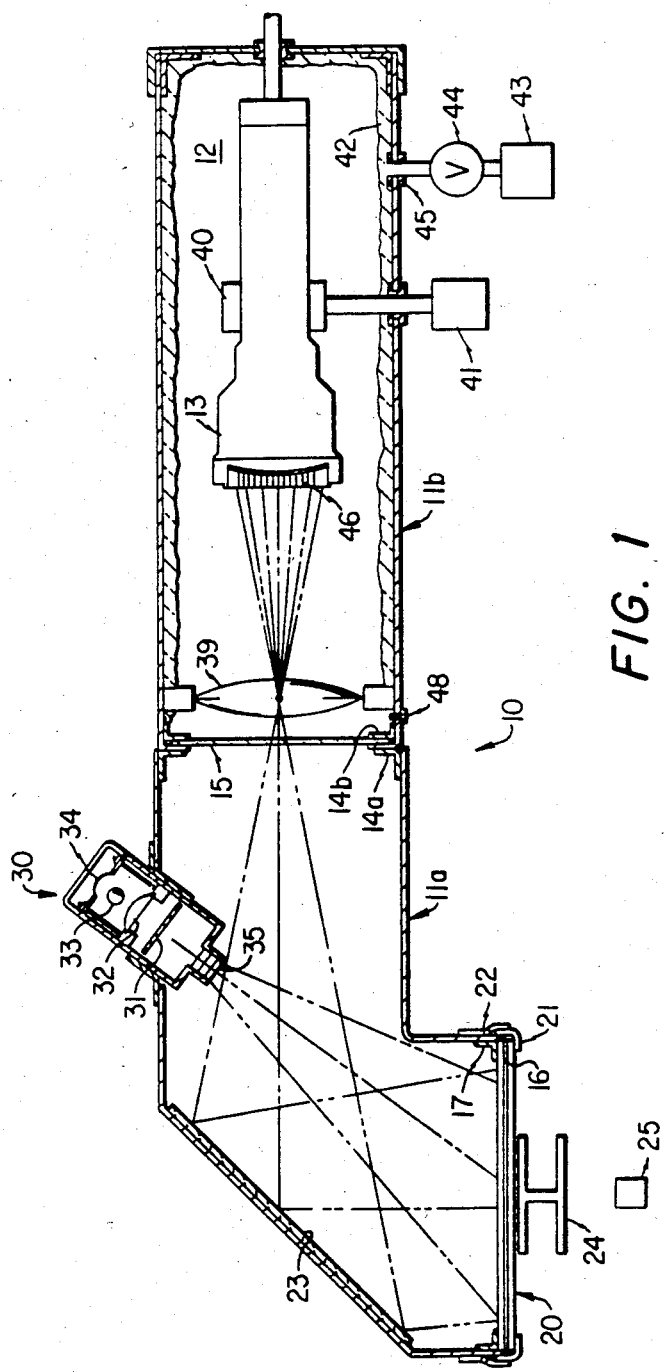
FIG. 1 is a partially diagrammatic, sectional view of the radiographic imaging system.

With initial reference to FIG. 1, radiographic system 10 comprises a housing consisting of first and second segments 11A and 11B. As will be understood more fully from the discussion, the first housing 11A is closed to prevent the entry of light, and the second housing, in addition to being closed, defines a substantially gas impervious chamber 12. The second housing segment 11B is of elongated configuration, and is of a sufficiently large diameter to accommodate a low-light-sensitive television camera 13. Camera 13 is mounted (by internal spiders or other mounting means, not shown) coaxially within the housing segment 11B, and with its optical input 46 directioned toward the first housing segment 11A. The camera 13 is a beam scanning camera having a semi-conductor target screen, and is suitably of the silicon intensified camera type (SIT); alternatively, other electronic scanning cameras may be employed such as the secondary emission charged coupled device (CCD), or charge injected device (CID) types. An example of a commercially available silicon intensified camera is manufactured by Arvin Diamond Corporation company as Model No. 6073B.

The first and second housing segments 11A, 11B are connected by means such as flanges 14A, 14B affixed within abutting eves portions of the respective housings, bolted or otherwise connected. A transparent, suitable glass plate 15 is sealingly mounted across an open end of the second housing segment 11B in front of the camera 13 permitting the passage of light to the camera input screen 46, as will be described in more detail hereinbelow. The first housing segment 11A is preferably generally L-shaped, having a perpendicularly facing window 16 at its end opposite the second housing segment 11B.

A flange 17 is mounted peripherally within the opening 16 and a radioluminescent screen structure 20 is fitted within the opening 16 against the internally mounted flange 17. An outer molding frame member 21 is detachably affixed to the housing segment 11A around the opening 16, the housing being suitably provided with latch mechanisms 22 permitting convenient fastening of the frame member 21 against the radioluminescent or phosphorescent imaging screen 20 which in turn is in intimate contact with the internal molding 17, whereby extraneous light is kept from the housing segment 11A. At the end of the housing segment 11A above the opening 16, a mirror 23 is mounted exending along a plane skewed by 45 degrees from the longitudinal axis of the housing and from an axis perpendicular to the plane of the screen structure 20, whereby images produced on the radioluminescent screen 20 are reflected by the mirror along the longitudinal axis of the housings 11A, 11B, and toward the camera 13. A workpiece 24 is positioned closely adjacent the radioluminescent screen 20 between the screen 20 and a source of radiation 25, the source 25 suitably being a source of or thermal neutron radiation, or low level or high level X-radiation, preferably emitted from means as from essentially a point source, for providing as sharp a shadowradiograph as possible upon the radiolumunescent screen 20. Preferably, as suggested above, the source 25 may be a non-isotopic, portable neutron generator as disclosed in U.S. Pat. No. 4,300,054, which produces a collimated beam of thermal neutrons directioned toward the screen.

A test pattern projector 30 is mounted above the screen within the first housing segment 11A and is directioned to form a projected image upon the inner side of the radioluminescent screen 20. As will be understood from the description of the operation of the system, the system preferably includes such a projection system because at low flux levels, the very low levels of scintillations produced on the screen 20 are not sufficient to permit adjustment of the focus current and target bias voltages during opeation of the camera. The test pattern projected on the screen is of sufficient intensity to permit convenient adjustment of both focus current and bias voltage, for subsequent use with the radiation source (without the projected image). The test pattern projector 30 includes a test pattern transparency 31, a condensing lens 32 being positioned between the transparency and a projection lamp 33 positioned in front of a projection mirror 34. Projection lens system 35 is directioned toward the radioluminescent screen 20. The housing of the test pattern projector 30 is removably affixed rough an opening formed in the upper portion of the first housing segment 11A by means of a flange structure 36, which may be bolted to the housing.

The television camera 13, in the preferred embodiment of the system, is cooled to reduce to the greatest extent possible any noise. As shown diagrammatically in FIG. 1, the tube 13 is preferably fitted within a cooling ring 40, the cooling ring 40 being mounted circumferentially of the target section of the camera, as will be more fully described hereinbelow with reference to FIG. 2, for maintaining the target preferably at temperatures in the range −15° to −40° C. The cooling ring 40 may comprise an annulus through which cryogenic, liquid nitrogen is circulated from a source, represented at 41, external ofhe housing segment 11B. Alternatively, the cooling ring 40 may comprise a Peltier junction device powered electrically. The second housing segment 11B is preferably insulated by insulation 42 formed on its inner wall surfaces. The interior 12 of the second housing segment 11B is preferably maintained as a moisture-free environment to prevent condensation upon the television tube 13, and a lens structure 39 positioned between the television tube input and the glass plate 15, as will be more fully described hereinbelow. For preventing condensation on the camera 13 or lens system 39, the interior of the second housing segment 11B may be evacuated, or preferably, charged with a drying agent such as nitrogen from source indicated at 43. Suitably, the nitrogen source 43 or other dry non flammable, electrically insulating gas communicates through valve 44 through tubing conducted through fitting 45 mounted within a suitable opening formed in the wall of the housing segment, and an outlet 48 is incorporated into the opposite end of the housing segment 11B. Prior to use of the system 10, outlet 48 is opened and nitrogen or other gas is permitted to flow through the inlet formed through fitting 45 for a period of time sufficient to remove most of the air and moisture from within the housing chamber 12 and charge the chamber with nitrogen. Subsequently, the chamber 12 is pressurized to approximately 6 psi, after which valve 44 is closed. It has been found in our experiments that such a charge is sufficient for preventing condensation on the camera tube 13 and optics 39 over an extended period of time of, for example, several months, with no need for further charge.

Figure 2:
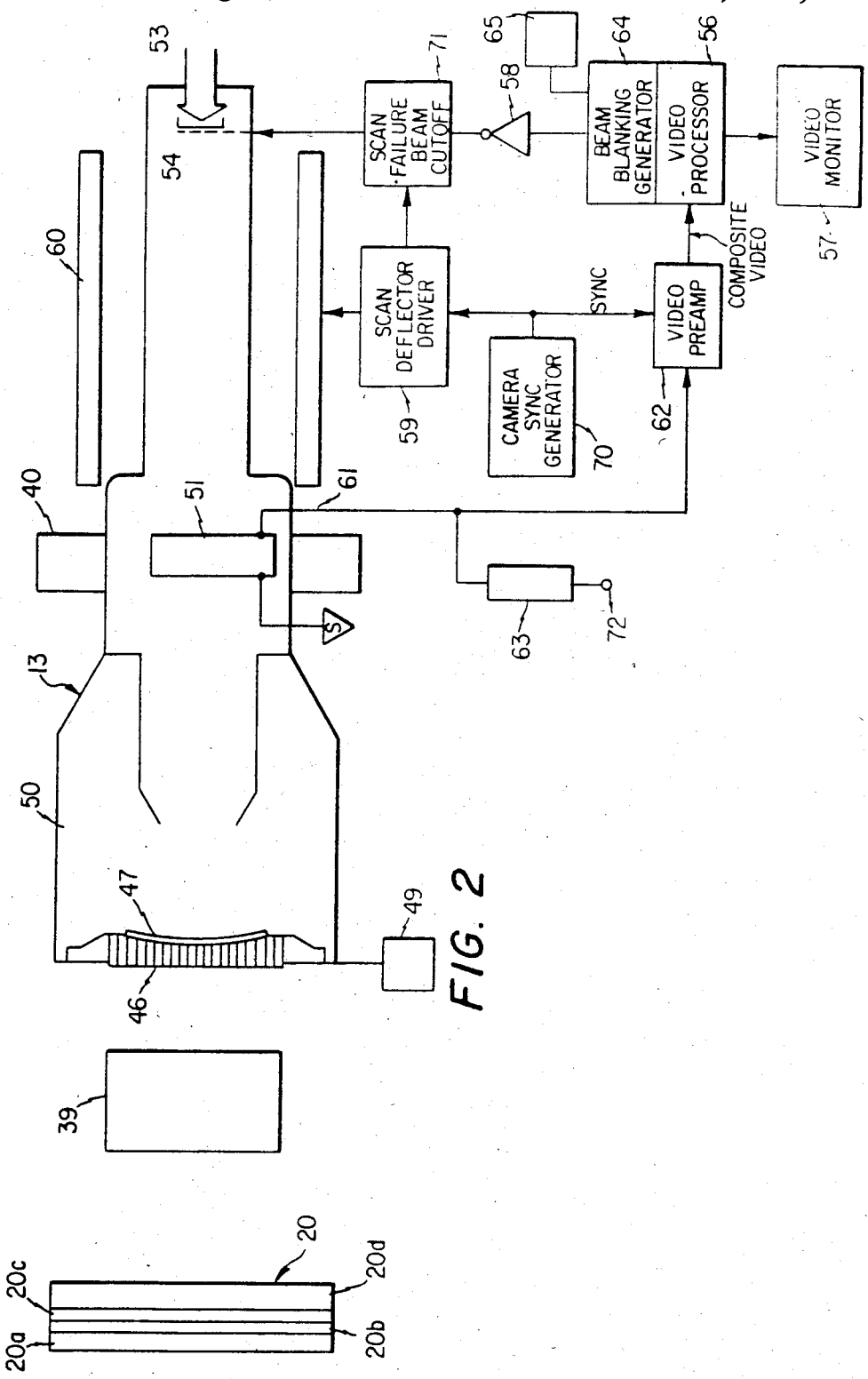
FIG. 2 is a diagrammatic representation of the video tube, in combination with the beam blanking, video processing, and video monitoring circuitry.

With reference now to FIG. 2, the optics and circuitry of the system are shown diagrammatically in somewhat greater detail. An important feature of the invention is the combination of a high output, radioluminescent screen structure 20 with a sensitive, low-noise camera 13 upon which light scintillations are gathered and integrated internally by means of target blanking. It should be understood that, in contrast with prior systems, target blanking is not employed for increasing image intensity, but is instead employed for statistical purposes, i.e., for accumulating sufficient scintillation information to form a radiographic image between electron beam raster scanning of the target to provide an adequate image. The light emitting, radioluminescent screen structure 20 includes an outer plate 20A of a material as transparent as possible to the radiation employed, but which is opaque to light. It is typically of aluminum, or of another material of a low "Z" number and low thermal neutron absorption characteristics. For convenience, a sealing layer 20B, of aluminum foil, is suitably employed adjacent the aluminum plate 20A to protect the phosphorescent, and more particularly, radioluminescent layer 20C. The phosphor layer 20C is suitably coated or deposited on a substrate 20D, which is of a transparent material such as glass. Alternatively, the phosphorous layer 20C can be deposited on the interior surface of the initial, outer plate 20A, with or without a protective glass plate 20D.

The system differs from prior systems in its use of a relatively high intensity radioluminescent layer 20C on the imaging screen, which permits the use of a relatively lower gain camera 13, and in the integration of scintillations on the target during the blanking periods. Preferably, the phosphor layer consists of a thin layer of a non-radioactive isotope of lithium in lithium fluoride, suitably combined with zinc sulfide, deposited on the substrate. In prior art systems, lithium-based phosphor layers have been used for gross, low resolution imaging purposes, but they inherently produce light scattering and diffusion, when subjected to radiation, which has in the past prevented their use in normal or high resolution imaging. In the present system, the prior difficulties are eliminated by the use of a very thin layer of the material, of about 0.025 inches or less, and preferably of about 0.020 inches or less. The lithium powder is mixed with a lithium binder material. Suitably the neutron-to-light radiophosphorescent convert material consists of a mixture of lithium fluoride and zinc sulfide powders mixed with a binder material, preferably one which also contains lithium, or the powder is otherwise held in place on the substrate by a thin transparent coating material. It is desirable to limit the quantity of binder materials to appoximately 10–15% by weight for providing maximum light output. Although various methods are known and utilized for laying materials in a thin film on a substrate, e.g. thin film chromotography, colloidal suspension in a settling tank etc., a recommended method is to form a suspension of the powder mixture in liquid solution containing a small quantity of the binder materials and then apply the resulting slurry to the substrate by "painting" or loading the substrate with the material, and then drawing a blade or knife-like edge such as a "doctors bar" across the surface to spread the material uniformly across the substrate. In order to maintain uniform thickness, the substrate must be flat, and rigidly attached to a machined flat surface. Coating thickness can be controlled to within 0.001" using this technique. As previously suggested, thin coatings of, for example, about 0.010 to 0.020 inches have been satisfactory, and preferably 0.012" to 0.025" coatings are employed.

When used with neutron radiation, the neutron particles react with the lithium to produce alpha particles by nuclear conversion of the lithium molecule, and the alpha particle reacts with the zinc sulfide to produce a scintillation of light energy. The lithium flouride component is thus a conversion element, for converting radiation to alpha particles, and the zinc sulphide component is a light producing element for producing light from alpha energy, for laying the material in a thin film on the substrate at a nominal thickness of 0.01 inches to 0.02 inches. The phosphor radioluminescent layer 20C is thus of importance as a radiation conversion material for converting the radiation received into low level, visible light radiation.

Lens structure 43 is an objective lens structure positioned to form an image of the phosphor layer 20C on the input fiber optic screen 46 of the camera. The camera tube 13 itself includes a fiber optic based "lens" input section 46 having a concave, inner photo imaging layer 47, which converts light derived from the scintillations into electron energy which are accelerated through an intensifying section 50 to the camera target 51 by means of an electric potential field. The target 51 comprises a a semiconductor, suitably silicon structure. Cooling ring 40 preferably maintains the target at a low temperature of $-15°$ C. to $-40°$ C., sufficient to minimize background noise and distortion during blanking periods. As is generally known by those in the art, such tubes 13 incorporate a raster scanning section, represented diagrammatically at 53, and typically employ a blanking grid 54 for imparting a blanking bias preventing scanning of the target 51 in the event of failure of the raster scanning circuitry (for the purpose of preventing damage to the target 51) by extended bombardment of a fixed location on the target 51 by the electron beam. The camera assembly typically includes internal circuitry for effecting the raster scanning, including the raster generator and scanning circuitry. Such internal raster scanning circuitry is generally operated in response to an internal sync generator 70 to provide television scanning of the target by the electron beam. A video or image processing unit 56, suitably a unit of the type manufactured by the Quantex Corporation as Model No. DS-20, is employed for generating beam blanking, timing and synchronization signals, and for storing, processing, and providing playback of video displays. Its output is fed to a video monitor unit 57 for permitting monitoring of images accumulated through integration of one or more successive frames of scanning. An internal timing and control circuit in the beam blanking generator portion of the picture processor 56 generates timing signals, which are logic signals of a selected time period. The logic signals are fed through a logic driver 58, suitably an open collector, TTL driver employed to increase the power of the blanking signal and invert it prior to its application to the scan failure beam cutoff circuit 71 and subsequently to the camera 13. The beam blanking generator portion 57 of the processing circuitry may be adjusted to vary the blanking period; during application of a blanking signal to the grid 54, the electron scanning beam is biased off. During the blanking period electron charge is stored in the silicon target in a pattern corresponding to the image which is scentillating on the radioflourescent screen.

At the completion of the blanking time interval, the electron beam is unbiased and allowed to scan the target surface 51 as steered by the deflection driver 59, including the raster generator, which is typically connected to deflection yokes 60 external of the tube. The deflection driver 59 is synchronized with an output signal from the camera sync geneator 70 and with the storage of video information derived from the target potential output 61. The target output, derived from 61, is amplified by a video preamp unit 62 and fed to the video processor 56. A load resistor 63 connected between the target output 61 and a target power supply 72 and imparts a bias to the target.

The video processor 56 serves to accumulate frames generated over a period of time during the non-blanking periods and provides an output to the video monitor 57 which is of high resolution, sufficient to permit evaluation of finely detailed internal faults in the specimens under examination. The image processor thus periodically activates the electron beam generator, reads resulting images, and processes the images for integrating sequential frames and averaging the frames, for improving clarity, and then continually reads out the processed image to the monitor. Typically, the electron scanning beam is blanked for a large portion of the inspection time. For example, the period of image storage may be on the order of 100 times greater than the scanning period; in some, low level radiation inspection, there may be even longer periods of storage relative to the scanning cycle period, depending upon the scintillation output.

The very low levels of energy produced by scintillations on phosphor screens from thermal neutron radiation or low level X-radiation have not been previously employed for the accumulation of statistical information on a semiconductor target during blanking periods, and the low level of energies presents problems with respect to the biasing and focusing of the camera tube 13. For this reason, the test pattern projector 30 (FIG. 1) is initially employed for adjusting the bias.

Thus, an important feature of the invention is its ability to store and accumulate statistically significant scintillation information on the target 51 within the tube 13 wherein the electron charge storage pattern builds up on the semiconductor target screen from individual scintillation events over a period of time until a statistically satisfactory image may be scanned, rather than being derived from external circuitry. This permits the use of a camera tube 13 which is of relatively inexpensive, rugged construction in comparison with those employing multiple intensfication sections, and thereby minimizes noise and distortion which typically results from the use of multiple stages of light intensification. Thus, the combination of the high output phosphor screen with the blanking of the target scanning produce high resolution images with components of moderate cost and complexity. An important advantage of the apparatus is its ability to produce clear images from low levels of radiation and its ability to produce images derived from both X-ray and N-ray sources without changing the internal configuration of the apparatus, that is, without changes of the structure of the phosphor screen or the camera, etc. Extremely clear images are obtained at very low radiation levels. In our experiments, satisfactory high resolution radiographic images have been produced derived from thermal neutrons radiation levels, for example, of about 500 neutrons per square cm. per second or greater, and with X-radiation of very low and very high levels (e.g., from 40 KEV, at 0.5 ma, at 30 inches, to 10 MEV). Moreover, images are obtained from such various radiation sources without mechanical modification of the camera lens system, or screen.

The test pattern projector 30, in combination with the radioluminescent screen 20 facing inwardly within a closed housing segment 11A, permits accurate, convenient focusing, both mechanically, i.e., by positioning lens 43, relative to the camera 13, and by adjustment of the target bias, and camera electronic focus, prior to actual radiography operations.

While only one embodiment of the invention, together with modifications thereof, has been described in detail herein and shown in the accompanying drawing, it will be evident that various further modifications are possible in the arrangement and construction of its components without departing from the scope of the invention.

What is claimed is:

1. A radiographic inspection system for producing a shadowgraoh or transmission image of an object to be inspected, comprising:

radiation means for directing radiation through the object;

a radioluminescent screen structure positioned to receive the radiation directioned through the object, the screen structure including a lithium based phosphorescent means for producing a scintillation shadowgraph pattern in response to impingement on the screen structure of the radiation directioned through the object;

a television camera for successively generating frames of video data during respective frame cycles, the camera having its optical input section directioned toward the radioluminescent screen, and having a semi-conductor target means for forming charge patterns corresponding to the scintillation patterns produced on the phosphorescent screen for producing shadowgraph images of the object, the television camera further including raster scanning means for scanning the semi-conductor target during respective frame cycles to generate an output signal corresponding to the charge pattern formed on the semi-conductor target;

means for controlling the raster scanning means for preventing scanning of the target during a blanking period extending continuously during a plurality of successive frame cycles to thereby accumulate an enhanced level of charge on the target derived from the scintillations on the phosphorescent screen, the accumulated charge representing a pattern corresponding to a shadowgraph image of the object, the control means being further operative for permitting scanning of the target, susequent to the blanking period for reading the charge accumulated during the blanking period; and means for processing information read from sequential raster scans of the target, subsequent to respective blanking periods, and for producing a television display corresponding to the shadowgraph scintillation pattern.

2. The apparatus of claim 1, wherein localized cooling means are provided for cooling the semiconductor target region of the camera for minimizing system noise during the period in which charge patterns derived from the phosphor scintillations are being accumulated, the localized cooling means being mounted adjacent the target.

3. The apparatus of claim 2, wherein a housing is provided for enclosing the television camera, the camera having an optical input section and a grid section, and wherein the localized cooling means is mounted within the housing, adjacent the camera tube at a location spaced between its optical input section and the grid section and is operable to cool the semi-conductor target region of the camera tube within the housing.

4. The apparatus of claim 3, wherein the localized cooling means is operable for cooling the interior of the housing.

5. The apparatus of caim 4, further comprising means for charging the interior of the housing with a drying agent.

6. The apparatus of claim 5, wherein the drying agent is nitrogen or $SF_6$.

7. The apparatus of claim 2, the camera having first and second end portions, the localized cooling means comprising an annular cooling member mounted circumferentially of the camera tube and adjacent the target.

8. The apparatus of claim 1, wherein a housing means is provided for supporting the radioluminescent screen structure in a plane which is displaced from and parallel to the optical axis of the television camera, and wherein a reflecting means is positioned within the housing means for reflecting scintillation patterns from the prosphor screen toward the television camera, wherein a test pattern projector means is positioned within the housing in alignment with the radioluminescent screen structure for projecting an image on the screen structure within the housing, the optical axis of the lens of the camera extending between the phosphor screen and the test pattern projector.

9. The apparatus of claim 1, wherein means are provided for forming a test pattern on the radioluminescent screen structure for permitting selection of appropriate bias and focus of the television camera for forming a high resolution image of the scintillation pattern derived from the neutron source.

10. The apparatus of claim 9, wherein the means for forming a test pattern on the radioluminescent screen structure comprises a projector means, directed toward the screen structure, for projecting an image in optical focus on the screen structure.

11. Radiographic imaging means comprising:
radiographic means for irradiating a workpiece;
radioluminescent means for conversion of radiation received from said radiographic means for producing a shadowgraphic or transmission scintillation pattern derived from radiation through and around the workpiece;
television camera means successively generating frames of video data during respective frame cycles, for producing a television image of the scintillation pattern, the television camera means having a semi-conductor target; and
means for controlling the raster scanning means for preventing scanning of the target during a blanking period extending continuously during a plurality of successive frame cycles thereby to accumulate an enhanced charge on the target derived from the scintillations on the phosphorescent screen, and representing a pattern corresponding to a shadowgraph image of the object, the control means being further operative for permitting scanning of the target during a nonblanking period after the blanking period for reading the charge accumulated during the blanking period.

12. The apparatus of claim 11, wherein the radioluminescent means includes a layer of lithium fluoride based phosphorescent material of a thickness less than about 0.04 inches.

13. The apparatus of claim 12, wherein the radioluminescent layer is of a thickness between about 0.01 inches and about 0.02 inches.

14. The apparatus of claim 13, wherein the phosphorescent material is zinc sulfide.

15. The apparatus of claim 11, wherein the radioluminescent layer comprises lithium fluoride in combination with a phosphorescent material.

16. The apparatus of claim 15, wherein the radioluminescent layer comprises lithium fluoride and zinc sulfide mixed with a binder which binder contains lithium powder.

17. The apparatus of claim 15, wherein the radioluminescent layer is supported by a glass substrate directioned toward the television camera, the camera being directioned toward the radioluminescent layer, through the glass substrate.

18. The radiographic imaging systems of claim 11, wherein the radiographic imaging means comprises means for generating thermal neutron radiation.

19. The apparatus of claim 18, wherein the radiographic means includes a non-isotopic radiation generator means.

20. The apparatus of claim 19, wherein the radiation means includes positioning means means for positioning the radiation generator means in alignment with the object and the phosphorescent material, the object being aligned between the radiation means and the phosphorescent material.

21. The apparatus of claim 20, the positioning means including directionable boom means for positioning the radiation generator means in alignment with the object and the phophorescent material.

22. The apparatus of claim 18, wherein the means for generating thermal neutron radiation includes radiation generating means and means for terminating the generation of neutron radiation.

23. A method of forming a television, radiographic image of a workpiece, comprising;
providing a radiofluorescent seen having radiation conversion means for causing alpha particles to be emitted upon bombardment of the screen by radiation; and having phosphorescent means for emitting scintillations of light in response to the emission of alpha particles; directing radiation through a workpiece and toward the screen for producing a scintillation shadowgraph pattern on the screen, providing a television camera directioned toward the screen, the camera generating frames of video data, during successive frame cycles, the camera further having a semiconductor target means for producing a charge pattern corresponding to the scintillation patterns, and raster target scanning means; and controlling scanning of the semiconductor target for preventing scanning of the semiconductor target during a blanking period extending continuously during a plurality of successive frame cycles thereby accumulating an enhanced charge pattern on the semiconductor target, and controlling the raster target scanning means after the blanking period for reading charge accumulated during the blanking period.

24. The apparatus of claim 23, wherein the radiation source is a source of thermal neutron radiation.

25. A radiographic inspection system for producing a shadowgraph or transmission image of an object to be inspected, comprising:
radiation means for directing thermal neutron radiation through the object;
a radioluminecent screen structure positioned to receive the neutron radiation directed through the object, the screen structure including a lithium based phosphorescent means for producing a scintillation shadowgraph pattern in response to impingement on the screen structure of neutrons directed through the object;
a television camera having an optical input section directioned toward the radioluminescent screen, and having a semiconductor target means for forming charge patterns corresponding to the scintillation patterns produced on the phosphorescent screen, and raster scanning means for scanning the semiconductor target during respective successive frame cycles to generate an output signal corresponding to the charge pattern formed on the semiconductor target;
means for controlling the raster scanning means for interrupting scanning of the target at selected intervals extending during a period corresponding to a plurality of successive frame cycles for permitting the accumulation of a charge pattern corresponding to the shadowgraph image of the object, and for subsequently permitting scanning of the target during nonblanking periods;

means for processing the information read from seqeuntial raster scans of the target during a plurality of nonblanking periods each subsequent to a respective blanking period and for producing a television display corresponding to the shadowgraph scintillation pattern; and means for forming a test pattern on the radioluminescent screen structure for permitting selection of appropriate bias and focus of the television camera for forming a high resolution image of the scintillation pattern derived from the neutron source.

26. The system of claim 25 wherein a test pattern projector means is positioned within a housing in alignment with the radioluminescent screen structure, the optical axis of the lens of the camera extending between the phosphor screen and the test pattern projector.

27. A radioluminescent screen comprising:
a substrate;
a lithium fluoride based phosphor layer deposited on said substrate;
means disposed adjacent said phosphor layer for sealing phosphor layer; and
plate means disposed adjacent said sealing means for receiving incident radiation.

28. The screen of claim 27 wherein said substrate comprises glass material.

29. The screen of claim 28 wherein said plate means comprises aluminum material.

30. The screen of claim 29 wherein said sealing means comprises aluminum foil material.

31. The screen of claim 30 wherein said phosphor layer includes a layer of lithium fluoride based phosphorescent material of a thickness less than about 0.025 inches.

32. The screen of claim 31, wherein said lithium fluroide-based phosphor layer comprises a layer of less than about 0.020 inches.

33. The screen of claim 30 wherein said phosphor layer includes a combination of an alpha emissive lithium flouride material and a light emitting means responsive to said alpha emissions produced by said lithium flouride materal.

34. The screen of claim 33, wherein said light emitting means comprises a zinc sulphide powder.

35. The screen of claim 27, wherein said phosphor layer comprises lithium fluoride and zinc sulfide mexed with a binder material, the binder material constituting 15 percent of less, by weight, of the phosphor layer.

36. The screen of claim 27, wherein said phosphor layer comprises lithium fluoride and zinc sulfide mixed with a binder material which also contains a lithium material.

* * * * *